United States Patent [19]

Youssefyeh et al.

[11] Patent Number: 4,935,511
[45] Date of Patent: Jun. 19, 1990

[54] BENZOXAZINE AND BENZOXAZEPINE CARBOXAMIDE 5-HT$_3$ ANTAGONISTS

[75] Inventors: Raymond D. Youssefyeh, Princeton Junction, N.J.; Jeffrey C. Pelletier, Lansdale; Henry F. Campbell, North Wales, both of Pa.

[73] Assignee: Rorer Pharmaceutical Corporation, Fort Washington, Pa.

[21] Appl. No.: 412,768

[22] Filed: Sep. 26, 1989

[51] Int. Cl.$^5$ .................. A61K 31/55; A61K 31/535; C07D 265/36; C07D 267/14
[52] U.S. Cl. ..................................... 540/552; 544/105
[58] Field of Search ............. 540/552; 514/211, 230.5; 544/105

[56] References Cited

U.S. PATENT DOCUMENTS 4,857,517 8/1989 Youssefyeh et al. ................ 514/161
4,859,683 8/1989 Youssefyeh et al. ................ 546/112

OTHER PUBLICATIONS

Chem. Abstract, vol. 109:160437v (1988), Kaneko.

*Primary Examiner*—Mukund J. Shah
*Assistant Examiner*—Phil Datlow
*Attorney, Agent, or Firm*—James A. Nicholson; Imre (Jim) Balogh

[57] ABSTRACT

This invention relates to benzoxazine and benzoxazepine carboxamide compounds which exhibit 5-HT$_3$ antagonist properties including CNS, anti-emetic and gastric prokinetic activity and which are void of any significant D$_2$ receptor binding affinity. This invention also relates to pharmaceutical compositions and methods for the treatment of gastrointestinal and mental disorders using said compounds.

10 Claims, No Drawings

BENZOXAZINE AND BENZOXAZEPINE CARBOXAMIDE 5-HT₃ ANTAGONISTS

FIELD OF THE INVENTION

This invention relates to benzoxazine and benzoxazepine carboxamide compounds which exhibit 5-HT$_3$ antagonist properties including CNS, anti-emetic and gastric prokinetic activity and which are void of any significant D$_2$ receptor binding affinity. This invention also relates to pharamceutical compositions and methods for the treatment of gastrointestinal and mental disorders using said compounds.

5-Hydroxytryptamine, abbreviated "5-HT", is commonly known as serotonin. Serotonin is found throughout the body including the gastrointestinal tract, platelets, spleen and brain, appears to be involved in a great number of physiological processes such as neurotransmission at certain neurones in the brain, and is implicated in a number of central nervous system (CNS) disorders. Additionally, serotonin appears to act as a local hormone in the periphery; it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors have been identified and the following assignment of receptors has been proposed; D-receptors are 5-HT$_2$-receptors; M-receptors are termed 5-HT$_3$-receptors; and all other receptors, which are clearly not 5-HT$_2$ or 5-HT$_3$, should be referred to as 5-HT$_1$-like.

5-HT$_3$-receptors have been located in non-neurological tissue, brain tissue, and a number of peripheral tissues related to different responses. It has been reported that 5-HT$_3$-receptors are located on peripheral neurones where they are related to serotonin's (excitatory) depolarizing action. The following subtypes of 5-HT$_3$ receptor activity have been reported: action involving postganglionic sympathetic and parasympathetic neurones, leading to depolarization and release of noradrenaline and acetylcholine, respectively (5-HT$_{3B}$ subtype); action on enteric neurones, where serotonin may modulate the level of acetylcholine (5-HT$_{3C}$ subtype): and action on sensory nerves such as those involved in the stimulation of heart nerve endings to produce a reflex bradycardia (5-HT$_{3A}$ subtype), and also in the perception of pain.

Highly selective 5-HT$_3$-antagonists have been shown to be very effective at controlling and preventing emesis (vomiting) induced by chemotherapy and radiotherapy in cancer patients. The anti-emetic effects of 5-HT$_3$-antagonists in animals exposed to cancer chemotherapy or radiation are similar to those seen following abdominal vagotomy. The antagonist compounds are believed to act by blocking 5-HT$_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an axon reflex mechanism, thus providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific 5-HT$_3$ receptors on the primary afferent neurones.

5-HT$_3$-antagonists are also reported to exert potential antipsychotic effects, and are believed to be involved in anxiety. Although not understood well, the effect is believed to be related to the indirect blocking of serotonin 5-HT$_3$-mediated modulation of dopamine activity.

Many workers are investigating various compounds having 5-HT$_3$-antagonist activity.

REPORTED DEVELOPMENTS

The development of 5-HT$_3$ agents originated from work carried out with metoclopramide (Beecham's Maxolon, A. H. Robins' Reglan), which is marketed for use in the treatment of nausea and vomiting at high doses. Metoclopramide is a dopamine antagonist with weak 5-HT$_3$-antagonist activity, which becomes more prominent at higher doses. It is reported that the 5HT$_3$ activity and not the dopamine antagonism is primarily responsible for its anti-emetic properties. Other workers are investigating this compound in connection with the pain and vomiting accompanying migraine.

Merrel Dow's compound MDL-72222 is reported to be effective as an acute therapy for migraine, but toxicity problems have reportedly ended work on this compound. Currently four compounds, A. H. Robins' Zacopride, Beecham's BRL-43694, Glaxo's GR-38032F and Sandoz' ICS-205-930 are in clinical trials for use in chemotherapy-induced nausea and vomiting. GR-38032F is also in clinical trials in anxiety and schizophrenia, and reportedly, Zacopride in anxiety, while ICS-205-930 has been shown to be useful in treating carcinoid syndrome.

Compounds reported as gastroprokinetic agents include Beecham's BRL-24924, which is a serotonin-active agent for use in gut motility disorders such as gastric paresis, audition reflux esophagitis, and is known to have also 5-HT$_3$-antagonist activity.

Metoclopramide, Zacopride, Cisapride and BRL-24924 are characterized by a carboxamide moiety situated para to the amino group of 2-chloro-4-methoxy aniline. BRL-43694, ICS-205930, GR-38032F and GR-65630 are characterized by a carbonyl group in the 3-position of indole or N-methyl indole. MDL-72222 is a bridged azabicyclic 3,5-dichlorobenzoate, while Zacopride, BRL-24924, BRL-43694 and ICS-205930 have also bridge azabicyclic groups in the form of a carboxamide or carboxylic ester.

Bicyclic oxygen containing carboxamide compounds wherein the carboxamide is ortho to the cyclic oxygen moiety are reported to have antiemetic and antipsychotic properties in EPO Publ. No. 0234872.

Dibenzofurancarboxamides and 2-carboxamide-substituted benzoxepines are reported to have 5HT$_3$-antagonist and gastroprokinetic activity in copending application Ser. Nos. 152,112, now Pat. No. 4,857,517, 152,192, now Pat. No. 4,859,683, 168,824, and 277,611, allowed, all of which are assigned to the same assignee as the present application.

SUMMARY OF THE INVENTION

This invention relates to the compounds having 5-HT$_3$ antagonist activity described by general Formula I and to therapeutic composition comprising as active ingredient a compound of Formula I:

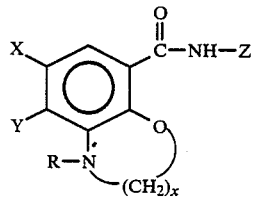

Formula I

Where:
X is
  hydrogen,
  halo,
  sulfamyl,
  alkylsulfamyl or
  alkylsulfonyl;
Y is
  hydrogen,
  amino,
  mono- or di-alkylamino or
  halo;
Z is

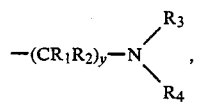

3-quinuclidine,
  4-quinuclidine,
  4-(1-azabicyclo[3.3.1]nonane),
  3-(9-methylazabicyclo[3.3.1]-nonane),
  7-(3-oxo-9-methylazabicyclo[3.3.1]nonane) or
  4-[3-methoxy-1-(3-[4-fluorophenoxy]propyl)piperidine];
R, R$_1$, R$_2$, R$_3$ and R$_4$ are independently:
  hydrogen or
  alkyl;
x is 2 or 3;
y is 1 to 4;
and pharmaceutically acceptable salts thereof.

This invention relates also to pharmaceutical compositions including an effective therapeutic amount of the aforementioned benzobicyclic carboxamide compound and therapeutic methods for the treatment of a patient suffering from gastrointestinal and/or psychochemical imbalances in the brain by administering said pharmaceutical composition.

DETAILED DESCRIPTION

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

The chemical structures for the Z groups defined above are presented below.

| | |
|---|---|
| 3-quinuclidine | 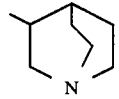 |
| 4-quinuclidine | 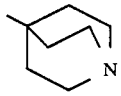 |
| 4-(1-azabicyclo-[3.3.1]nonane) | 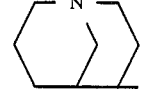 |
| 3-(9-methylazabicyclo[3.3.1]nonane) | 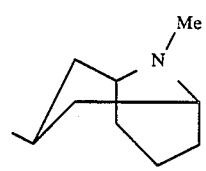 |
| 7-(3-oxo-9-methylazabicyclo[3.3.1] nonane) | 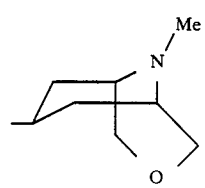 |
| 4-[3-methoxy-1-(3-[4-fluorophenoxy]propyl)piperidine] | 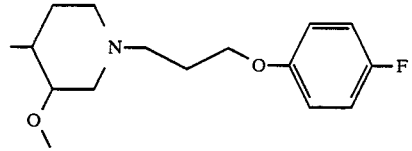 |

The following nomenclature is used in the description of this invention;

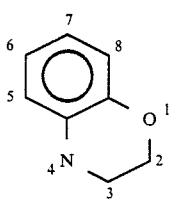 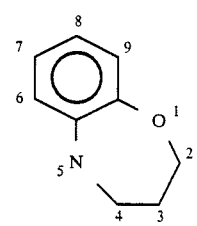

Certain of the compounds of the present invention may exist in enolic or tautomeric forms, and all of these forms are considered to be included within the scope of this invention.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Preferred compounds of this invention include those compounds of Formula I where Z is

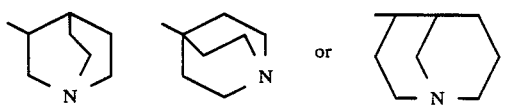

More preferred compounds include those where x is 3, R is hydrogen and Z is 3-quinuclidine.

Most preferred compounds are described where:
X is halo and Y is hydrogen;
Y is amino or loweralkylamino and X is hydrogen; or
X is halo and Y is amino;
especially when halo is chloro or bromo and loweralkyl is methyl.

The present compounds may be prepared by the following general procedure:

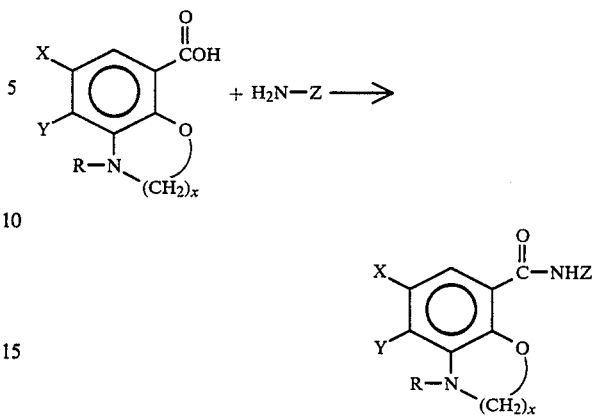

Condensation of a substituted 1,4-benzoxazin-8-carboxylic acid or substituted 1,5-benzoxazepin-9-carboxylic acid, acid halide or ester with an amine of the formula ZNH₂ results in the corresponding substituted benzoxazin-8-carboxamide or substituted benzoxazepin-9-carboxamide.

In general this reaction may be carried out at 0° C. by adding ethylchloroformate to a reaction mixture of the acid in chloroform in the presence of triethylamine. This is then reacted with the amine of the formula ZNH₂ to obtain the desired product. Condensation also may be carried out in the presence of a dehydrating catalyst such as carbodiimide in a solvent at normal temperatures.

The carboxylic acid starting materials and derivatives thereof for the above mentioned reaction are also novel compounds and comprise part of the present invention. These materials comprise the appropriately substituted 1,4-benzoxazin and 1,5-benzoxazepin carboxylic compound corresponding to the appropriate carboxamide compound of Formula I.

The carboxylic acid intermediate compounds may be prepared from known starting materials commercially available or may be prepared by known methods.

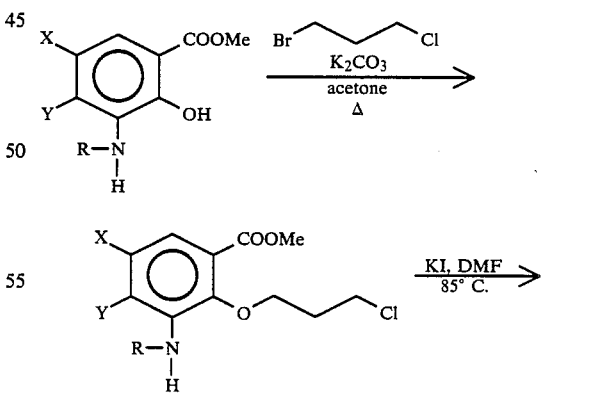

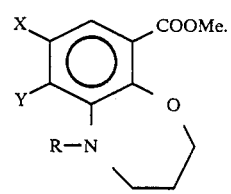

Refluxing of the substituted 3-aminosalicylate with bromochloropropane in the presence of $K_2CO_3$ in acetone followed by treatment with KI in a DMF medium at 85° C. provides the desired 1,5-benzoxazepin ester which then can be hydrolyzed to the acid and reacted with the $ZNH_2$ amine to obtain the desired product.

In a similar manner the 1,4-benzoxazine ester may be prepared.

The compounds of this invention may contain at least one asymmetric carbon atom such as the 3-quinuclidinyl compounds or when $R_1 \neq R_2$. As a result, the compounds of Formula I may be obtained either as racemic mixtures or as individual enantiomers. When two asymmetric centers are present the product may exist as a mixture of two diastereomers. The product may be synthesized as a mixture of the isomers and the desired isomer separated by conventional techniques such as chromatography or fractional crystallization from which each diastereomer may be resolved. On the other hand, synthesis may be carried out by known stereospecific processes using the desired form of the intermediate which would result in obtaining the desired specificity.

It is convenient to carry out condensation of the intermediate carboxylic acids mentioned above with the amines of the formula $H_2N$-Z using the sterospecific materials. Accordingly, the acid may be resolved into its stereoisomers prior to condensation with resolved amine. For example, resolution of 3-aminoquinuclidine results in S(—)3-aminoquinuclidine and R(+)3-aminoquinuclidine. When S(—)3-aminoquinuclidine is reacted as above with 7-chloro-2,3,4,5-tetrahydro-1,5-benzoxazepin-9-carboxylic acid then the product obtained is 7-chloro-9-[N-(1-azabicyclo[2.2.2]octan-3(S)-yl]-2,3,4,5-tetrahydro-1,5-benzoxazepincarboxamide.

Further is racemic 3-aminoquinuclidine is converted to a benzamide derivative it can also be separated into its enantiomers using chiral HPLC. The benzamide is hydrolyzed to the amine. The desired resultant resolved products may then be coupled as desired to obtain the amide.

In a similar manner the remaining various stereospecific compounds may be prepared.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practice of this invention. A further useful reference is *Enantiomers, Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromotography.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, maleic acid, oxalic acid, succinic acid, glycolic acid, lactic acid, salicylic acid, benzoic acid, nicotiinic acid, phthalic acid, stearic acid, oleic acid, abietic acid, etc.

We have found that the compounds of this invention have gastric prokinetic and anti-emetic properties and lack $D_2$ receptor binding activity. As such they possess therapeutic value in the treatment of upper bowel motility and gastroesophageal reflux disorders. Further, the compounds of this invention may be useful in the treatment of disorders related to impaired gastrointestinal motility such as retarded gastric emptying, dyspepsia, flatulence, aesophageal reflux, peptic ulcer and emesis. The compounds of this invention exhibit 5-$HT_3$ antagonism and are considered to be useful in the treatment of psychotic disorders such as schizoprenia and anxiety and in the prophylaxis treatment of migraine and cluster headaches. We have further found that these compounds are selective in that they have little or no dopaminergic antagonist activity.

Various tests in animals can be carried out to show the ability of the compounds of this invention to exhibit pharmacological responses that can be correlated with activity in humans. These tests involve such factors as the effect of the compounds of Formula I on gastric motility, emesis, selective antagonism of 5-$HT_3$ receptors and their $D_2$ dopamine receptor binding properties.

It has been found that the compounds of this invention when tested in the above variety of situation show a marked activity.

One such test is the "Rat Gastric Emptying: Amberlite Bead Method". This test is carried out as follows:

The test is designed to assess the effects of a test agent on gastric emptying of amberlite beads in the rat. The procedure is a modification of those used in L. E. Borella an W. Lippman (1980) *Digestion* 20: 26-49.

PROCEDURE

Amberlite beads are placed in a phenol red solution and allowed to soak for several hours. Phenol red serves as an indicator, changing the beads from yellow to purple as their environment becomes more basic. After soaking, the beads are rinsed with 0.1NaOH to make them purple and then washed with deionized water to wash away the NaOH.

The beads are filtered several times through 1.18 and 1.4 mm sieves to obtain beads with diameters in between these sized. This is done using large quantities of deionized water. The beads are stored in saline until ready to use.

Male Sprague-Dawley rats are fasted 24 hours prior to the study with water ad libitum. Rats are randomly divided in treatment groups with an N or 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite beads intragastrically. The beads are delivered via a 3 inch piece of PE 205 tubing attached to a 16 gauge tubing adapter and syringe. A small piece of PE 50 tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads ±S.E.M. is determined for each treatment group. The percent change from control is calculated as follows:

$$\frac{\text{Mean Control Group} - \text{Mean Test Agent Group}}{\text{Mean Control Group}} \times 100.$$

Statistical significance may be determined using a t-test for independent samples with a probability of 0.05 or less considered to be significant.

In order to demonstrate the ability of the compounds of this invention as anti-emetic agents the following test for "Cisplatin-Induced Emesis in the Ferret" may be used. This test is a modified version of a paper reported by A. P. Florezyk, J. E. Schurig and W. T. Brodner in *Cancer Treatment Reports:* Vol. 66, No. 1. January 1982.

Cisplatin had been shown to cause emesis in the dog and cat. Florcyzk, et al. have used the ferret to demonstrate the same effects.

PROCEDURE

Male castrated, Fitch ferrets, weighing between 1.0 and 1.5 kg have an Indwelling catheter in place in the jugular vein. After a 2-3 day recovery period, the experimental procedure is begun.

30 minutes prior to administration of cisplatin, ferrets are dosed with the compound in 0.9% saline (i.v.) at a dose volume of 2.0 ml/kg.

45 minutes after administration of cisplatin, ferrets are again dosed with the 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of cisplatin administration is taken as time zero. Ferrets are observed for the duration of the experiment (4 hours). The elapsed time to the first episode is noted and recorded, as are the total number of periods of emesis.

An emetic (vomiting) episode is characterized by agitated behavior, such as pacing around the cage and rapid to and from movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 DOPAMINE RECEPTOR BINDING ASSAY

The D-2 dopamine receptor binding assay has been developed with slight modifications using the method of Ian Cresse, Robert Schneider and Solomon H. Snyder, *Europ. J. Pharmacol.* 46: 377-381 (1977). Spiroperidol is a butyrophenone neuroleptic whose affinity for dopamine receptors in brain tissue is greater than that of any other known drug. It is a highly specific D-1 dopamine (non-cyclase linked) receptor agent with $K_1$ values of 0.1-0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleus (corpus striatum) is used as the receptor source because it contains the highest density of dopamine receptors in the brain and periphery.

PROCEDURE

Male Charles-River rats weighing 250-300 g are decapitated and their brains removed, cooled on ice, and caudate dissected immediately and frozen on dry ice. Tissue can be stored indefinitely at −70° C. For assay caudate is homogenized in 30 ml of tris buffer (pH 7.7 at 25° C.) using the polytron homogenizer. The homogenate is centrifuged at 40,000 g (18,000-19,000 RPM in SS-34 rotor) for 15 minutes. Pellet is resuspended in fresh buffer and centrifuged again. The final pellet is resuspended in 150 volumes of assay buffer.

Specific $^3$H-spiroperidol binding is assayed in a total 2 ml reaction volume consisting of 500 ml of caudate homogenate, 50 mM EDTA.2NA, 120 mM NaCl, 0.1% ascorbic acid, 0.4 nM $^3$H-spiroperidol and test compound or assay buffer. When catecholamines are included in the assay, 10 mM pargyline should be included in the reaction mixture to inhibit monoamine oxidase. Samples are incubated at 37° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 mM d(+) butaclamol is used to determine nonspecific binding. Filters are placed in vials containing 10 ml of Ecoscint phosphor, shaken for 30 minutes and dpm determined by liquid scintillation spectrophotometery using a quench curve. Proteins are determined by the method of Bradford, M. Anal. Biochem. 72, 248(1976) using Bio-Rad's coomassie blue G-250 dye reagent. Bovine gamma globulin supplied by BIO-RAD is used as the protein standard.

BEZOLD-JARISCH EFFECT IN ANESTHETIZED RATS

Male rats 260-290 g are anesthetized with urethane 1.25 g/kg$^{-1}$ i.p., and the trachea cannulated. The jugular vein is cannulated for intravenous (i.v.) injection drugs. Blood pressure is recorded from a cannula in the left carotid artery and connected to a haparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injection of 5-HT. The effect of the compound on the 5-HT-evoked bradycardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 s trains with a maximally-effective voltage (20 V at 10 Hz). Pulse frequency may vary from 5-30 Hz and frequency-response curves are constructed before and 10 minutes after i.v. injection of a single dose of compound.

The results of these above tests indicate that the compounds for this invention exhibit a valuable balance between the peripheral and central action of the nervous system and may be useful in the treatment of disorders related to impaired gastro-intestinal motility such as gastric emptying, dyspepsia, flatulence, esphogal reflux and peptic ulcer and in the treatment disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes; intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelation capsules, or it may be compressed into tablets, or it may be incorporated directly with the food of the diet. For oral therapeutic administration, the active compound may be incorporated with excipient and used in th form of ingestive tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, lginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperiotoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparations of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, ployol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agent delaying absorption, for example, aluminum monostearate and galatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 50 mg/kg of body weight per day and higher although it may be administered in several different dosage units from once to several times a day. Higher dosages are required for oral administration.

The compounds of this invention may be prepared by the following representative examples.

EXAMPLE 1

Methyl 2-methoxy-4-amino-5-chlorobenzoate hydrochloride

A suspension of 30 g (0.15 mol) of 2-methoxy-4-amino-5-chlorobenzoic acid in 500 ml methanol is cooled to 0° and the mixture treated with gaseous HCl for 30 minutes. After all the acid dissolves the solution is evaporated to dryness to obtain methyl 2-methoxy-4-amino-5-chlorobenzoate hydrochloride which is used directly in the next step.

When 2-methoxy-4-amino-5-chlorobenzoic acid in the above procedure is replaced by the compounds of Table I below, then the corresponding product of Table II below is prepared:

Table I 2-methoxy-5-chlorobenzoic acid,
2-methoxy-5-bromobenzoic acid,
2-methoxy-5-sulfamylbenzoic acid,
2-methoxy-5-methylsulfamylbenzoic acid,
2-methoxy-5-methylsulfonylbenzoic acid,
2-methoxy-4-dimethylamino-5-chlorobenzoic acid,
2-methoxy-4-methylamino-5-chlorobenzoic acid,
2-methoxy-4-aminobenzoic acid,
2-methoxy-4,5-dichlorobenzoic acid,
2-methoxy-4-amino-5-bromobenzoic acid

TABLE II

Methyl 2-methoxy-5-chlorobenzoate
Methyl 2-methoxy-5-bromobenzoate
Methyl 2-methoxy-5-sulfamylbenzoate
Methyl 2-methoxy-5-methylsulfamylbenzoate
Methyl 2-methoxy-5-methylsulfonylbenzoate
Methyl 2-methoxy-4-methylamino-5-chloro hydrochloride
Methyl 2-methoxy-4-dimethylamino-5-chloro hydrochloride
Methyl 2-methoxy-4-aminobenzoate hydrochloride
Methyl 2-methoxy-4,5-dichlorobenzoate
Methyl 2-methoxy-4-amino-5-bromobenzoate hydrochloride

EXAMPLE 2

4-Amino-5chlorosalicylic acid

A suspension of 37 g (0.15 mol) of methyl 2-methoxy-4-amino-5-chlorobenzoate hydrochloride in 500 ml methylene chloride is stirred at 25° C. To this is added 600 ml (0.60 mol) of BBr₃ in CH₂Cl₂ gradually until the ester dissolves. After 24 hours stirring a ppt. forms on the side of the flask. This mixture is poured into rapidly stirring ice water (700 ml). Aqueous NaOH (5.5N, 600 ml) is poured in to the flask to dissolve the ppt. The water organic layer forms a ppt. and this mixture is stirred and cooled in an ice bath and treated with the NaOH solution cautiously. The ppt. dissolves and the organic layer is separated. The aqueous layer is washed with CH₂Cl₂ (200 ml) and then cooled to 0° and treated with concentrated HCl with stirring. A colorless ppt. forms which is filtered, washed (H₂O) and air dried to obtain 4-amino-5-chlorosalicylic acid which is used directly in the next step.

When methyl 2-methoxy-4-amino-5-chlorobenzoate hydrochloride in the above example is replaced by the compounds of Table II, Example 1, then the products of Table III below are obtained.

TABLE III 5-chlorosalicylic acid
5-bromosalicylic acid
5-sulfamylsalicylic acid
5-methylsulfamylsalicylic acid
5-methylsulfonylsalicylic acid
4-methylamino-5-chlorosalicylic acid
4-dimethylamino-5-chlorosalicylic acid
4-aminosalicylic acid
4,5-dichlorosalicylic acid
4-amino-5-bromosalicylic acid

EXAMPLE 3

Methyl 4-amino-5-chlorosalicylate hydrochloride

To 300 ml of methanol is added 30 ml of thionylchloride and stirred at 0° C. To this is added 26 g (0.14 mol) of 4-amino-5-chlorosalicylic acid and refluxed for 18 hours. The mixture is clear and evaporated to dryness to obtain methyl 4-amino-5-chlorosalicylate hydrochloride which is then used directly in the next step.

When 2-methoxy-4-amino-5-chlorosalicylic acid in the above example is replaced by the compounds of Table III, Example 2, then the products of Table IV below are obtained.

TABLE IV

Methyl 5-chlorosalicylate
Methyl 5-bromosalicylate
Methyl 5-sulfamylsalicylate
Methyl 5-methylsulfamylsalicylate
Methyl 5-methylsulfonylsalicylate
Methyl 4-methylamino-5-chlorosalicylate hydrochloride
Methyl 4-dimethylamino-5-chlorosalicylate hydrochloride
Methyl 4-aminosalicylate hydrochloride
Methyl 4,5-dichlorosalicylate
Methyl 4-amino-5-bromosalicylate hydrochloride

EXAMPLE 4

Methyl 2-acetoxy-4-acetylamino-5-chlorobenzoate

A mixture of 10.9 g (54 mmol) of methyl 4-amino-5-chlorosalicylate hydrochloride diluted with 250 ml pyridine is stirred at 0° C. and treated with 17 g (0.22 mol, 16 mls) of acetyl chloride over a 10 minute period. A ppt. begins to form and the mixture is stirred 30 minutes longer at 0° C. This is then treated with 30 ml H₂O and stirred for 5 minutes after which time the ppt. dissolves. The mixture is diluted with CH₂Cl₂ (500 ml), washed with H₂O (500 ml) and 10% HCl (4×300 ml). The organic layer is dried (MgSO₄) and evaporated to dryness to obtain crude product which is recrystallyzed from ethylacetate-hexane to obtain pure methyl 2-acetoxy-4-acetylamino-5-chlorobenzoate; m.p. 134°–36° C.

When methyl 4-amino-5-chlorosalicylate hydrochloride in the above example is replaced by the compounds of Table IV, Example 3, then the products of Table V below are prepared.

TABLE V

Methyl 2-acetoxy-5-chlorobenzoate
Methyl 2-acetoxy-5-bromobenzoate

Methyl 2-acetoxy-5-sulfamylbenzoate
Methyl 2-acetoxy-5-methylsulfamylbenzoate
Methyl 2-acetoxy-5-methylsuulfonylbenzoate
Methyl 2-acetoxy-4-methylamino-5-chlorobenzoate
Methyl 2-acetoxy-4-dimethylamino-5-chlorobenzoate
Methyl 2-acetoxy-4-acetylaminobenzoate
Methyl 2-acetoxy-4,5-dichlorobenzoate
Methyl 2-acetoxy-4-acetylamino-5-bromobenzoate

EXAMPLE 5

Methyl 3-nitro-4-acetylamino-5-chlorosalicylate

To a mixture of 90 ml concentrated $HNO_3$ and 10 ml concentrated $H_2SO_4$ cooled to $-10°$ C. is added portionwise over 5 minutes 10.9 g (38.2 mmol) methyl 2-acetoxy-4-acetylamino-5-chlorobenzoate. The mixture is stirred another 5 minutes and poured into ice water (400 ml). The ppt. which forms is filtered, washed ($H_2O$) and dried to obtain methyl 3-nitro-4-acetylamino-5-chlorosalicylate; m.p. 166°–69° C.

When methyl 2-acetoxy-4-acetylamino-4-chlorobenzoate in the above example is replaced by the compounds of Table V, Example 4, then the products of Table VI below are prepared.

TABLE VI

Methyl 3-nitro-5-chlorosalicylate
Methyl 3-nitro-5-bromosalicylate
Methyl 3-nitro-5-sulfamylsalicylate
Methyl 3-nitro-5-methylsulfamylsalicylate
Methyl 3-nitro-5-methylsulfonylsalicylate
Methyl 3-nitro-5-methylamino-5-chlorosalicylate
Methyl 3-nitro-4-dimethylamino-5-chlorosalicylate
Methyl 3-nitro-4-acetylaminosalicylate
Methyl 3-nitro-4,5-dichlorosalicylate
Methyl 3-nitro-4-acetylamino-5-bromosalicylate

EXAMPLE 6

Methyl 3-nitro-4-amino-5-chlorosalicylate

Sodium (3.8 g, 0.17 m) is dissolved in 150 ml methanol and to this is added methyl 3-nitro-4-acetylamino-5-chlorosalicylate (5 g, 17 mmol) under nitrogen. This mixture is then heated to reflux overnight. The mixture is then cooled to 20° C. and poured into a rapidly stirring mixture of ice and 10% HCl (650 ml). The ppt. which forms is filtered, washed with $H_2O$ and dried to obtain methyl 3-nitro-4-amino-5-chlorosalicylate as a yellow powder which is used directly in the next step.

When methyl 3-nitro-4-acetylamino-5-chlorosalicylate in the above example is replaced by:
methyl 3-nitro-4-acetylaminosalicylate or
methyl 3-nitro-4-acetylamino-5-bromosalicylate,
then the products prepared are:
methyl 3-nitro-4-aminosalicylate or
methyl 3-nitro-4-amino-5-bromosalicylate.

EXAMPLE 7

Methyl 3,4-diamino-5-chlorosalicylate

Methyl 3-nitro-4-amino-5-chlorosalicylate (4.1 g, 0.017 mmol) is hydrogenated at 45 initial psi in 450 ml ethanol for 30 minutes using 2.1 g of 10% Pt/C. The catalyst is then filtered (celite) and washed with ethylacetate (450 ml) and the filtrate evaporated in vacuo to give methyl 3,4-diamino-5-chlorosalicylate which is used directly in the next step.

When methyl 3-nitro-4-amino-5-chlorosalicylate in the above example is replaced by the compounds of Table VII below then the products of Table VIII below are prepared.

TABLE VII

Methyl 3-nitro-5-chlorosalicylate
Methyl 3-nitro-5-bromosalicylate
Methyl 3-nitro-5-sulfamylsalicylate
Methyl 3-nitro-5-methylsulfamylsalicylate
Methyl 3-nitro-5-methylsulfonylsalicylate
Methyl 3-nitro-4-methylamino-5-chlorosalicylate
Methyl 3-nitro-4-dimethylamino-5-chlorosalicylate
Methyl 3-nitro-4-aminosalicylate
Methyl 3-nitro-4,5-dichlorosalicylate
Methyl 3-nitro-4-amino-5-bromosalicylate

TABLE VIII

Methyl 3-amino-5-chlorosalicylate
Methyl 3-amino-5-bromosalicylate
Methyl 3-amino-5-sulfamylsalicylate
Methyl 3-amino-5-methylsulfamylsalicylate
Methyl 3-amino-5-methylsulfonylsalicylate
Methyl 3-amino-4-methylamino-5-chlorosalicylate
Methyl 3-amino-4-dimethylamino-5-chlorosalicylate
Methyl 3,4-diaminosalicylate
Methyl 3-amino-4,5-dichlorosalicylate
Methyl 3,4-diamino-5-bromosalicylate

EXAMPLE 8

Methyl 3'-chloropropoxy-3,4-diamino-5-chlorobenzoate

To a mixture of methyl 3,4-diamino-5-chlorosalicylate (3.3 g, 15 mmol) and $K_2CO_3$ (21 g, 0.15 mol) in 100 ml acetone is added 1,3-bromochloropropane (4.8 g, 30 mmol) while stirring vigorously, under nitrogen. This is heated at reflux for 12 hours, cooled, diluted with 350 ml $H_2O$ and extracted with 3×100 ml ether. The combined organic layers are dried over $MgSO_4$ and evaporated to dryness. The crude product is chromatographed on silica gel ($CHCl_3$-ethylacetate; 1:1) to obtain methyl 3'-chloropropoxy-3,4-diamino-5-chlorobenzoate which is used directly in the next step.

EXAMPLE 9

Methyl 6-amino-7-chloro-2,3,4,5-tetrahydro-1,5-benzoxazepin-9-carboxylate

A mixture of methyl 3'-chloropropoxy-3,4-diamino-5-chlorobenzoate (2.7 g, 9.2 mmol) and KI (3.1 g, 18 mmol), diluted with 40 ml DMF is heated to 85° C. under nitrogen atmosphere. After 3 hours, the mixture is cooled to 20° C. and partitioned between $H_2O$ (100 ml) and ether (100 ml). The aqueous layer is washed with ether (75 ml) and the combined ether layers are washed with water (8×100 ml), dried and evaporated to dryness to obtain a brown gum. The aqueous layer is extracted with $CH_2Cl_2$ (3×150 ml) which is dried and evaporated and the DMF is distilled off to leave a brown gum. The combined gums are chromatographed on silica gel ($CHCl_3$-ethyl acetate; 9:1) to obtain a light tan gum which crystallizes on standing to obtain methyl 6-amino-7-chloro-2,3,4,5-tetrahydro-1,5-benzoxazepin-9-carboxylate; m.p. 92°–95° C.

When 3,4-diamino-5-chlorosalicylate in Example 8 is replaced by the compounds of Table VIII, Example 7 and the procedures of Examples 8 and 9 are followed, then the compounds prepared are shown in Table IX below.

TABLE IX

Methyl 7-chloro-2,3,4,5-tetrahydro-1,5-benzoxazepin-9-carboxylate
Methyl 7-bromo-2,3,4,5-tetrahydro-1,5-benzoxazepin-9-carboxylate
Methyl 7-sulfamyl-2,3,4,5-tetrahydro-1,5-benzoxazepin-9-carboxylate
Methyl 7-methylsulfamyl-2,3,4,5-tetrahydro-1,5-benzoxazepin-9-carboxylate
Methyl 7-methylsulfonyl-2,3,4,5-tetrahydro-1,5-benzoxazepin-9-carboxylate
Methyl 6-methylamino-7-chloro-2,3,4,5-tetrahydro-1,5-benzoxazepin-9-carboxylate
Methyl 6-dimethylamino-7-chloro-2,3,4,5-tetrahydro-1,5-benzoxazepin-9-carboxylate
Methyl 6-amino-2,3,4,5-tetrahydro-1,5-benzoxazepin-9-carboxylate
Methyl 6,7-dichloro-2,3,4,5-tetrahydro-1,5-benzoxazepin-9-carboxylate
Methyl 6-amino-7-bromo-2,3,4,5-tetrahydro-1,5-benzoxazepin-9-carboxylate

EXAMPLE 10

6-Amino-7-chloro-2,3,4,5-tetrahydro-1,5-benzoxazepin-9-carboxylic acid

A solution of methyl 6-amino-7-chloro-2,3,4,5-tetrahydro-1,5-benzoxazepin-9-carboxylate (1.6 g, 6.3 mmol) in 40 ml of methanol is treated with KOH (0.49 g, 7.5 mmol) in 5 ml of $H_2O$. This is then heated to reflux for 16 hours. The methanol is then evaporated and the residue diluted to 35 mls with $H_2O$. The brown solution is stirred and cooled in an ice bath and treated with toluene sulfonic acid (1.7 g, 9 mmol). The resulting ppt. is filtered, washed with water and dried to obtain tan crude product. The mother liquor is extracted with $CHCl_3$ (2×20 ml) and dried ($MgSO_4$) and evaporated to dryness to obtain further crude product. Recrystallization from ethanol-ethyl acetate results in 6-amino-7-chloro-2,3,4,5-tetrahydro-1,5-benzoxazepin-9-carboxylic acid; m.p. 187°–89° C. dec.

When methyl 6-amino-7-chloro-2,3,4,5-tetrahydro-1,5-benzoxazepin-9-carboxylate in the above example is replaced by the compounds of Table IX, Example 9 then the products of Table X below are prepared.

TABLE X

7-Chloro-2,3,4,5-tetrahydro-1,5-benzoxazepin-9-carboxylic acid
7-Bromo-2,3,4,5-tetrahydro-1,5-benzoxezpin-9-carboxylic acid
7-Sulfamyl-2,3,4,5-tetrahydro-1,5-benzoxazepin-9-carboxylic acid
7-Methylsulfamyl-2,3,4,5-tetrahydro-1,5-benzoxazepin-9-carboxylic acid
7-Methylsulfonyl-2,3,4,5-tetrahydro-1,5-benzoxazepin-9-carboxylic acid
6-Methylamino-7-chloro-2,3,4,5-tetrahydro-1,5-benzoxazepin-9-carboxylic acid
6-Dimethylamino-7-chloro-2,3,4,5-tetrahydro-1,5-benzoxazepin-9-carboxylic acid
6-Amino-2,3,4,5-tetrahydro-1,5-benzoxazepin-9-carboxylic acid
6,7-Dichloro-2,3,4,5-tetrahydro-1,5-benzoxazepin-9-carboxylic acid
6-Amino-7-bromo-2,3,4,5-tetrahydro-1,5-benzoxazepin-9-carboxylic acid

EXAMPLE 11

6-Amino-7-chloro-9-[N-(1-azabicyclo[2.2.2.]octan-3-yl)]-2,3,4,5-tetrahydro-1,5-benzoxazepincarboxamide dihydrochloride To 6-amino-7-chloro-2,3,4,5-tetrahydro-1,5-benzoxazepin-9-carboxylic acid (1 g, 4.1 mmol) dissolved in 20 ml $CHCl_3$ and triethylamine (0.83 g, 8.2 mmol, 1.1 mls) chilled to −20° C. is added ethyl chloroformate (0.42 g, 3.8 mmol, 0.39 ml) and stirred for 1 hour. To this mixture is added 3-aminoquinuclidine (2.5 g, 13 mmol) and 5 ml saturated aqueous $K_2CO_3$ solution. Stirring is continued for another hour at −20° C. Water (20 ml) is added and the organic layer is separated and washed with $H_2O$ (4×25 ml), dried and evaporated to dryness. The residue is dissolved in $CHCl_3$ (20 ml) and evaporated to dryness four times to obtain 6-amino-7-chloro-9-[N-(1-azabicyclo[2.2.2.]octan-3-yl)]-2,3,4,5-tetrahydro-1,5-benzoxazepincarboxamide dihydrochloride; m.p. 229°–31° C.

When 6-amino-7-chloro-2,3,4,5-tetrahydro-1,5-benzoxazepin-9-carboxylic acid in the above example is replaced by the compounds of Table X, Example 10, then the products of Table XI below are prepared.

TABLE XI

7-Chloro-9-[N-(1-azabicyclo[2.2.2.]octan-3-yl]-2,3,4,5-tetrahydro-1,5-benzoxazepincarboxamide
7-Bromo-9-[N-(1-azabicyclo[2.2.2.]octan-3-yl]-2,3,4,5-tetrahydro-1,5-benzoxazepincarboxamide
7-Sulfamyl-9-[N-(1-azabicyclo[2.2.2.]octan-3-yl]-2,3,4,5-tetrahydro-1,5-benzoxazepincarboxamide
7-Methylsulfamyl-9-[N-(1-azabicyclo[2.2.2.]octan-3-yl]-2,3,4,5-tetrahydro-1,5-benzoxazepincarboxamide
7-Methylsulfonyl-9-[N-(1-azabicyclo[2.2.2.]octan-3-yl]-2,3,4,5-tetrahydro-1,5-benzoxazepincarboxamide
6-Methylamino-7-chloro-9-[N-(1-azabicyclo[2.2.2.]octan-3-yl]-2,3,4,5-tetrahydro-1,5-benzoxazepincarboxamide
6-Dimethylamino-7-chloro-9-[N-(1-azabicyclo[2.2.2.]octan-3-yl]-2,3,4,5-tetrahydro-1,5-benzoxazepincarboxamide
6-Amino-9-[N-(1-azabicyclo[2.2.2.]octan-3-yl]-2,3,4,5-tetrahydro-1,5-benzoxazepincarboxamide
6,7-Dichloro-9-[N-(1-azabicyclo[2.2.2.]octan-3-yl]-2,3,4,5-tetrahydro-1,5-benzoxazepincarboxamide
6-Amino-7-bromo-9-[N-(1-azabicyclo[2.2.2.]octan-3-yl]-2,3,4,5-tetrahydro-1,5-benzoxazepincarboxamide

EXAMPLE 12

When 3-aminoquinuclidine in Example 11 is replaced by S(−)3-aminoquinyclidine or R(+)3-aminoquinuclidine then the products prepared are 6-amino-7-chloro-9-[N-(1-azabicyclo[2.2.2.]octan-3(S)-yl]-2,3,4,5-tetrahydro-1,5-benzoxazepincarboxamide dihydrochloride and 6-amino-7-chloro-9-[N-(1-azabicyclo[2.2.2.]octan-3(R)-yl]-2,3,4,5-tetrahydro-1,5-benzoxazepincarboxamide dihydrochloride.

EXAMPLE 13

When 3-aminoquinuclidine in Example 11 is replaced by the compounds of Table XII below, then the products of Table XIII below are prepared.

TABLE XII

N,N-dimethylaminopropylamine
N,N-diethylaminopropylamine

N,N-dipropylaminopropylamine
N,N-dimethylaminoethylamine
3-Aminoquinuclidine
4-Aminoquinuclidine
4-Amino-1-azabicyclo[3.3.1.]nonane
3-Amino-9-methylazabicyclo[3.3.1]nonane
7-Amino-3-oxo-9-methylazabicyclo[3.3.1.]nonane
4-Amino-3-methoxy-1-(3-[4-fluorophenoxy]propyl)-piperidine

TABLE XIII

6-Amino-7-chloro-9-[N-(N'N'-dimethylaminopropyl)]-2,3,4,5-tetrahydro-1,5-benzoxazepinecarboxamide dihydrochloride 6-Amino-7-chloro-9-[N-(N'N'-diethylaminopropyl)]-2,3,4,5-tetrahydro-1,5-benzoxazepinecarboxamide dihydrochloride 6-Amino-7-chloro-9-[N-(N'N'-dipropylaminopropyl)]-2,3,4,5-tetrahydro-1,5-benzoxazepinecarboxamide dihydrochloride 6-Amino-7-chloro-9-[N-(N'N'-diproplaminoethyl)]-2,3,4,5-tetrahydro-1,5-benzoxazepinecarboxamide dihydrochloride 6-Amino-7-chloro-9-[N-(1-azabicyclo[2.2.2.]octan-3-yl)]-2,3,4,5-tetrahydro-1,5-benzoxazepinecarboxamide dihydrochloride 6-Amino-7-chloro-9-[N-(1-azabicyclo[2.2.2.]octan-4-yl)]-2,3,4,5-tetrahydro-1,5-benzoxazepinecarboxamide dihydrochloride 6-Amino-7-chloro-9-[N-(1-azabicyclo[3.3.1.]nonan-4-yl)]-2,3,4,5-tetrahydro-1,5-benzoxazepinecarboxamide dihydrochloride 6-Amino-7-chloro-9-[N-(9-methylazabicyclo[3.3.1]nonan-3-yl)]-2,3,4,5-tetrahydro-1,5-benzoxazepinecarboxamide dihydrochloride 6-Amino-7-chloro-9-[N-(3-oxo-9-methylazabicyclo[3.3.1.]nonan-7-yl)]-2,3,4,5-tetrahydro-1,5-benzoxazepinecarboxamide dihydrochloride 6-Amino-7-chloro-9-[N-(3-methoxy-1-(3-[4-fluorophenoxy]propyl)piperidin-4-yl)]-2,3,4,5-tetrahydro-1,5-benzoxazepinecarboxamide dihydrochloride

EXAMPLE 14

When the procedure of Example 11 is followed and 6-amino-7-chloro-1,5-benzoxazepin-9-carboxylic acid is replaced by the compounds of Table X, Example 10; and 3-aminoquinuclidine is replaced by S(−)3-aminoquinuclidine or R(+)3-aminoquinuclidine or the compounds of Table XII, Example 13, then the corresponding product is prepared.

EXAMPLE 15

When bromochloropropane of Example 8 is replaced by bromochloroethane and the procedures of Examples 8 and 9 are followed then the product prepared is methyl 5-amino-6-chloro-2,3-dihydro-3(H)-1,4-benzoxazin-8-carboxylate.

In a similar manner, when 1,3-bromochloropropane of Example 8 is replaced by 1,2-bromochloroethane and the procedures of Examples 8 and 9 are followed using the compounds of Table VIII, Example 7, then the corresponding benzoxazines are prepared.

EXAMPLE 16

When methyl 6-amino-7-chloro-2,3,4,5-tetrahydro-1,5-benzoxazepin-9-carboxylate of Example 10 is replaced by the benzoxazine-8-carboxylates of Example 15, then the corresponding benzoxazine-8-carboxylic acid is prepared.

EXAMPLE 17

When the procedure of Example 11 is followed and 6-amino-7-chloro-2,3,4,5-tetrahydro-1,5-benzoxazepin-9-carboxylic acid is replaced by the benzoxazine-8-carboxylic acids prepared by Example 16; and when 3-aminoquinuclidine is replaced by S(−)3-aminoquinuclidine or R(+)3-aminoquinuclidine or the compounds of Table XII, Example 13, then the corresponding compound is prepared.

We claim:
1. A compound of the formula

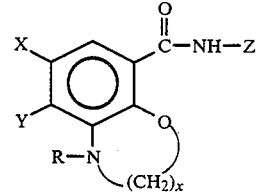

where:
X is
  hydrogen,
  halo,
  sulfamyl,
  alkylsulfamyl or
  alkylsulfonyl;
Y is
  hydrogen,
  amino,
  mono- or di-alkylamino or
  halo;
Z is

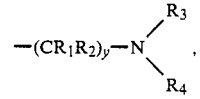

3-quinuclidine,
  4-quinuclidine,
  4-(1-azabicyclo[3.3.1]nonane),
  3-(9-methylazabicyclo[3.3.1]-nonane),
  7-(3-oxo-9-methylazabicyclo[3.3.1]nonane) or
  4-[3-methoxy-1-(3-[4-fluorophenoxy]propyl)piperidine];
R, $R_1$, $R_2$, $R_3$ and $R_4$ are independently:
  hydrogen or
  alkyl;
x is 2 or 3;
y is 1 to 4;
and pharmaceutically acceptable salts thereof.

2. A compound according to claim 1 where Z is

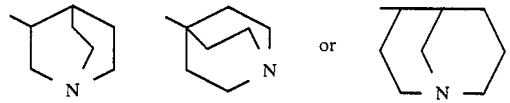

3. A compound according to claim 2 where x is 3, R is hydrogen and Z is 3-quinuclidine.

4. A compound according to claim 3 where 3-quinuclidine is in the S(−) form.

5. A compound according to claim 4 where X is halo and Y is hydrogen.

6. A compound according to claim 4 where Y is amino or loweralkylamino and X is hydrogen.

7. A compound according to claim 4 where X is halo and Y is amino.

8. A compound according to claim 7 which is 6-amino-7-chloro-9-[N-(1-azabicyclo[2.2.2.]octan-3(S)-yl]2,3,4,5-tetrahydro-1,5-benzoxazepincarboxamide and pharmaceutically acceptable salts thereof.

9. A compound according to claim 5 which is 7-chloro-9-[N-(1-azabicyclo[2.2.2.]octan-3(S)-yl)]2,3,4,5-tetrahydro-1,5-benzoxazepincarboxamide and pharmaceutically acceptable salts thereof.

10. A compound according to claim 2 which is 6-amino-7-chloro-9-[N-(1-azabicyclo[3.3.1]nonan-4-yl)]-2,3,4,5-tetrahydro-1,5-benzoxazepincarboxamide and pharmaceutically acceptable salts thereof.

* * * * *